United States Patent [19] … [11] Patent Number: 5,028,234
Schweitzer et al. … [45] Date of Patent: Jul. 2, 1991

[54] DENTAL TOOL

[76] Inventors: Glenn Schweitzer, 415 E. Elm St., Wheaton, Ill. 60181; Richard E. Jacky, 266 Hawthorne, Glen Ellyn, Ill. 60137

[21] Appl. No.: 380,486

[22] Filed: Jul. 17, 1989

[51] Int. Cl.⁵ ............................................. A61C 3/00
[52] U.S. Cl. .................... 433/147; 433/141
[58] Field of Search ............. 433/141, 142, 143, 146, 433/147, 164, 166

[56] References Cited

U.S. PATENT DOCUMENTS

| Re. 13,621 | 9/1913 | Kelly | 66/88 |
|---|---|---|---|
| 532,721 | 1/1895 | Dennis | 433/147 |
| 737,616 | 9/1903 | Harrell | 279/9 R |
| 971,382 | 9/1910 | Kelly | 433/144 |
| 1,003,213 | 9/1911 | Skinner | 433/143 |
| 1,039,235 | 9/1912 | Wiggins | 433/147 |
| 1,209,789 | 12/1916 | Wilson | 433/146 |
| 1,327,477 | 1/1920 | Ivory | 433/147 |
| 1,356,372 | 10/1920 | Wilson | 433/143 |
| 1,406,143 | 2/1922 | Bates | 433/147 |
| 1,586,302 | 5/1926 | Funk | 433/80 |
| 2,474,684 | 6/1949 | McCaughley | 15/172 |
| 3,660,902 | 5/1972 | Axelsson | 433/142 |
| 3,869,797 | 3/1975 | Malmin | 433/147 |
| 4,323,347 | 4/1982 | Weissman | 433/141 |
| 4,364,730 | 12/1982 | Axelsson | 433/141 |
| 4,552,531 | 11/1985 | Martin | 433/147 |
| 4,643,677 | 2/1987 | Kim | 433/164 |

FOREIGN PATENT DOCUMENTS 766532  6/1934  France .................. 433/164

Primary Examiner—Gene Mancene
Assistant Examiner—Michael Lynch
Attorney, Agent, or Firm—Hill, Van Santen, Steadman & Simpson

[57] ABSTRACT

A dental tool providing a sure grip handle connected at one end or both ends to a head for inserting tool parts such as brushes, the head and brushes disposed at an angle from the longitudinal axis of the handle, the head accepting tool parts into an aperture formed through the head. The centerline axis of the aperture being disposed at an angle from the longitudinal axis of the handle causes the axis of the tool part to be disposed at either an acute or obtuse angle from the longitudinal axis of the handle depending on which side of the aperture is used for tool part insertion. The aperture is formed in a manner to securely hold the tool part while allowing removability, either by opposing tapered ports through the head, or by a restricted orifice interior of the aperture.

21 Claims, 1 Drawing Sheet

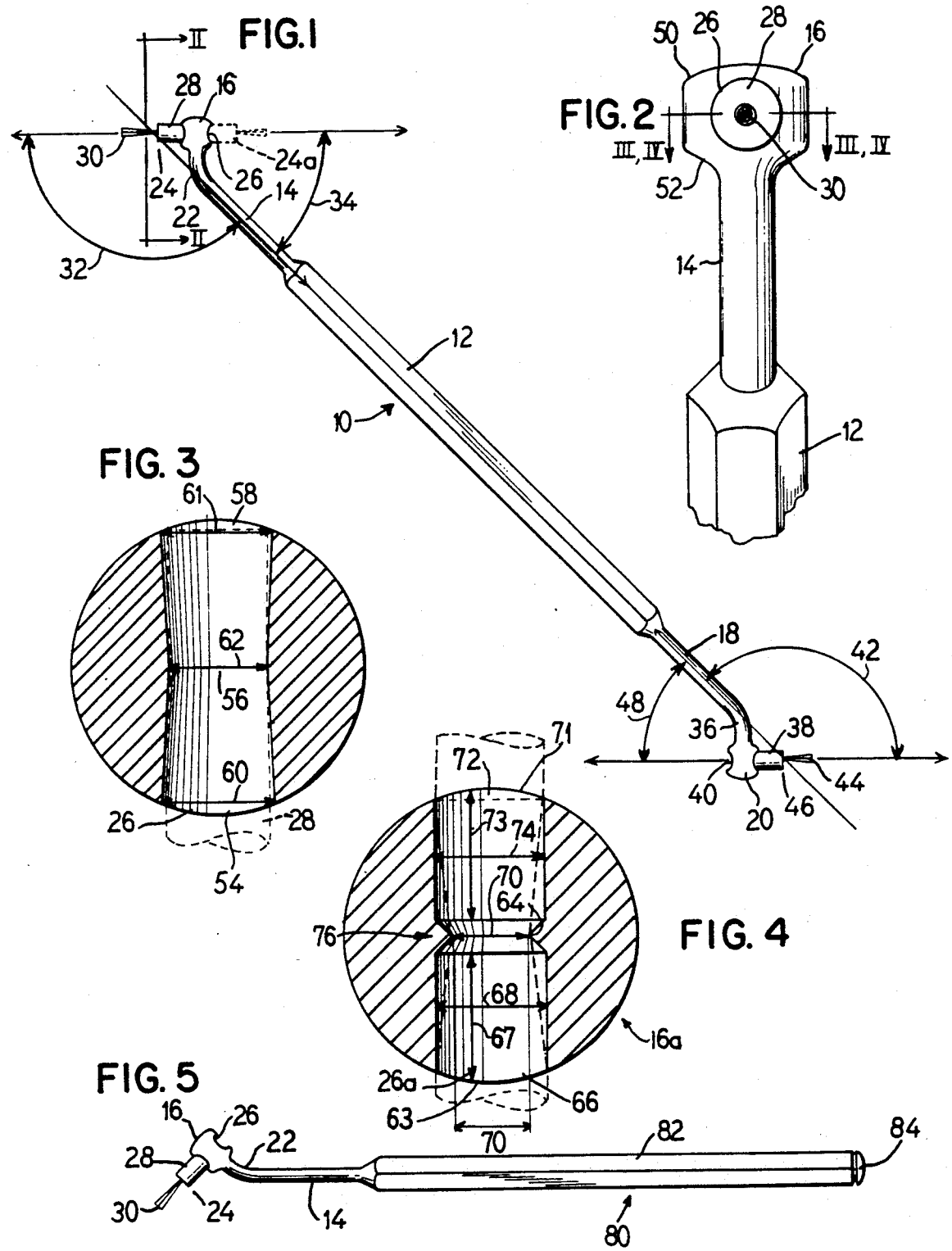

DENTAL TOOL

BACKGROUND OF THE INVENTION

This invention relates to a dental tool and more particularly to a dental tool having two operable ends with replaceable brushes mounted thereon.

Dental tools having brushes mounted on their ends are well known. U.S. Pat. No. 1,209,789 to W. E. Wilson discloses a dental instrument which can accept a brush at both ends. U.S. Pat. No. 971,382 and its reissue No. RE 13,621 to J. L. Kelly illustrate a dental handpiece with two ends angled relative to the handpiece and having an aperture at each end therethrough which is tapered to snugly receive a polishing insert. The provision of angled ends on dental handpieces appeared to be known and apertured ends for receiving inserts is also known. U.S. Pat. No. 1,209,789 to W. E. Wilson, U.S. Pat. No. 1,356,372 to J. L. Kelly, U.S. Pat. No. 1,003,213 to F. H. Skinner, U.S. Pat. No. 971,382 to J. L. Kelly and reissue Pat. No. 13,621 to J. L. Kelly all disclose a dental hand tool with angled ends and apertured ends for receiving inserts.

It would however be an improvement in the art to provide a dental tool which increased the possible orientations of inserts such as brushes at each end of the tool while still permitting the inserts to be removable and held in place firmly.

SUMMARY OF THE INVENTION

The present invention provides an improved dental tool in which one or both ends of the tool has at least two differently oriented apertures therein to receive an end of a removable tool part such as a brush. The dental tool embodied in the present invention is easy to hold and maneuver, difficult to drop, provides access to difficult to access areas of a patient's mouth, accepts a range of diameters of brush tip inserts, is of a one piece construction (less tool parts), and is constructed of a material suitable for sterilization processes.

BRIEF DESCRIPTION OF THE DRAWINGS

FIG. 1 is a plan View of a dental tool.

FIG. 2 is a partial sectional view generally along line II—II of FIG. 1.

FIG. 3 is a partial sectional view generally along line III—III of FIG. 2.

FIG. 4 is a partial sectional view generally along line IV—IV of FIG. 2, representing an alternate embodiment of a receiving head of the dental tool.

FIG. 5 is a plan view of an alternate embodiment of the present invention.

DETAILED DESCRIPTION OF THE PREFERRED EMBODIMENTS

FIG. 1 shows a dental tool generally at 10, including a handle 12, a first shaft 14, a first head 16, a second shaft 18, and a second head 20. The handle 12, has a generally hexagonal shape providing a secure means of grasping the handle 12 and preventing rotation of the handle 12 about its longitudinal axis during manipulations by a user. Other polygon shapes could also be used, such as triangular, square, etc. as well as a cylindrical shape, but preferably only with knurling. The handle 12 is connected at one handle end to a first end of the first shaft 14, and the first shaft 14 is connected at a second end, remote from the handle 12, to the first head 16. The handle 12 is connected at a second handle end to a first end of the second shaft 18, and the second shaft 18 is connected at a second end, remote from the handle 12, to the second head 20. The first shaft 14 is generally collinear with the longitudinal axis of the handle 12. However, a remote portion 22 of the first shaft 14 is angularly dislocated from the longitudinal axis of the handle 12, thus the first head 16 is offset from the longitudinal axis of the handle 12.

The first head 16 receives a tool part such as a first brush 24 in a first aperture or passage 26. The first brush 24, preferably comprises a compressible resilient base portion such as a compressible cylinder portion 28 and a bristle portion 30. The first aperture 26, extends throughout an entire depth of the first head 16. An alternate location of a tool part such as the first brush 24 is shown dashed and indicated by 24a. The brush 24a also comprises the cylinder portion 28 and the bristle portion 30. The brush 24a provides a different angular orientation with respect to the longitudinal axis of the handle 12 than would be obtained with the first brush 24.

The included angle 32 between an axis of the first brush, described vectorially along a centerline of the cylinder portion 28 in a direction from the first head 16 towards an extreme end of the bristle portion 30, and the longitudinal axis of the handle 12 described vectorially from the first shaft 14 towards the second shaft 18, is an obtuse angle. Alternatively, the included angle 34 between the longitudinal axis of the handle 12 described vectorially from the first shaft 14 towards the second shaft 18, and a centerline axis of the brush 24a, described vectorially in a direction along a centerline of the cylinder portion 28 from the first head 16 towards an extreme end of the bristle portion 30, is an acute angle. This feature of the first head 16, which permits alternate locations of the brush 24, 24a provides the user with flexibility to access difficult to access portions of a patient's mouth. Alternatively, the remote portion 22 could be a straight portion, included angles 32 and 34 could be 90° (not shown). This simple configuration is encompassed by the present invention.

Similar to the first shaft 14, the second shaft 18 includes an angled second remote portion 36, which connects to the second head 20, thus the second head 20 is offset from the longitudinal axis of the handle 12. A dental tool part such as a second brush 38 inserts into a second aperture or passage 40 extending throughout an entire depth of the second head 20. The second brush 38 may be similar or identical to the first brush 24. The included angle 42 between the longitudinal axis of the handle 12 described vectorially from the second shaft member 18 toward the first shaft member 14, and an axis of the second brush 38, the axis of the second brush 38 described vectorially from the second head 20 towards an extreme end of a second bristle portion 44, along a centerline of a second compressible cylinder portion 46 is an obtuse angle. With the second brush 38 placed into an opposite opening of aperture 40, thus in an alternate orientation described by a vector turned 180° from the axis of the brush 38 as described above, the alternate included angle 48 between the longitudinal axis of the handle 12 described vectorially from the second shaft member 18 toward the first shaft member 14, and a brush axis in the alternate orientation, would be an acute angle. This feature of the second head 20, which permits alternate locations of the second brush 38, forming either an acute or obtuse angle to the longitudinal axis of the handle 12, provides the user with flexibility to access difficult to access portions of a patient's mouth. Alternatively, the second remote portion 36 could be a straight portion and included angles 42 and 48 could be 90°. This configuration is encompassed by the present invention.

By providing two heads 18, 20 at opposite ends of dental tool 10, a user can install two different tool parts, one at each end, or use each end for a different service such as to apply two different materials to a tooth.

FIG. 2 shows the cylinder portion 28 of the brush 24 inserted snugly into the aperture 26 formed in the first head 16. The first head 16 comprises a solid cylindrical shape, although other shapes such as boxlike or spherical shapes are possible and encompassed by the present invention. A top portion 50 of the first head 16 comprises a shallow dome shape and a bottom portion 52 of first head 16 comprises a generally conical shape transitioning into first shaft 14.

FIG. 3 shows an internal structure of the first head 16. The cylinder portion 28 of the first brush 24 is shown dashed inside the aperture 26. The aperture 26 extends through an entire depth of the first head 16. A near side port or opening 54 is tapered toward a central location 56 approximately half way through the first head 16. An opposite side port or opening 58 is tapered towards the central location 56. The near side port 54 has an outward or maximum diameter 60 and the opposite side port 58 has an outward or maximum diameter 61. The outward diameters 60, 61, are slightly larger than the cylinder portion 28 to facilitate entry of the first brush 24, 24a. The central location 56 has a minimum diameter 62 which is slightly smaller than the cylinder portion 28. Since the cylinder portion 28 is compressible and resilient, it can be pressed into the central location 56 where it will be securely held. When either brush 24, 24a is fully inserted into the aperture 26, the first head 16 exerts a circumferential grip on the cylinder 28 due to gradually decreasing diameters approaching the minimum diameter 62, thus securing either first brush 24, 24a into the first head 16. The same method and arrangement is utilized to secure the second brush 38 into the second head 20, inserted into either end opening of second aperture 40.

It would also be possible to form the passage 26 with a constant diameter throughout with a separate means formed on one or the other of the passage 26 and the base portion 28 of the tool part to cause a removable gripping engagement between the base portion and the passage. The tapering of the passage from both ends thereof towards the central portion is only one means for accomplishing this function. Separate means formed on either the passage or the base portion, such as a tapering of the base portion or circumferential protrusions on one or both of the passages and base portion could also be utilized within the scope of this invention.

FIG. 4 shows an alternate embodiment of the first head 16, as alternate head 16a, wherein an alternate aperture 26a comprises a different configuration. The alternate aperture 26a proceeds from a near side 63 towards a central portion 64 with a first cylindrical bore 66 without taper. At a inward distance 67 somewhat less than a half depth of alternate head 16a, the first cylindrical bore 66, which has a diameter 68, tapers toward the central portion 64, to a minimum diameter 70. The alternate aperture 26a proceeds from an opposite side 71 towards the central portion 64 with a second cylindrical bore 72 without taper. At an inward distance 73 somewhat less than a half depth of alternate head 16a, the second cylindrical bore 72 with a diameter 74 tapers at the central portion 64 to the minimum diameter 70. The first cylindrical bore 66 from the near side and the second cylindrical bore 72 from the opposite side, meet at a central portion 64, have collinear centerlines, and define in the central portion an annular restricted orifice 76. The diameters 68, 74 are slightly larger than the cylinder portion 28, and the diameter 70 is slightly smaller than the cylinder portion 28. Thus either first brush 24, 24a can be readily inserted into the bores 66, 72, and when fully inserted are securely gripped by the restricted orifice 76. The alternate aperture 26a can also be used in lieu of the second aperture 40.

Both FIG. 3 and FIG. 4 show the apertures 26 and 26a as being through the entire depth of heads 16, 16a in a collinear fashion. This configuration presents a simple design which facilitates manufacturing, and is therefore the preferred embodiment. However, other orientations of apertures are possible. The near side port 54 and the opposite side port 58 need not be collinear or intersecting. Likewise, the first cylindrical bore 66 and the second cylindrical bore 72 need not be collinear or intersecting. Other orientations of the ports 54, 58 and the bores 66, 72 are encompassed by the present invention. Similarly, the invention is not limited to only two bores in each head.

The ports 54, 58 and the bores 66, 72 are indicated as generally cylindrical. Although a cylindrical shape is the preferred embodiment for machining ease, other shapes such as squared slots, channels, etc. are possible. Likewise, the compressible base portions 28, 46 of the brushes 24, 24a, 38 are shaped cylindrically in the preferred embodiment, but can be shaped as bars or any other shape complementary to the ports 54, 58 or the bores 66, 72. Such variations in shape for the ports 54, 58 or the bores 66, 72 and compressible bases 28, 46 are encompassed by the present invention.

Another feature of the present invention is the compatibility of the apertures 26, 26a, 40 to accept tool parts of varying widths or diameters. Because the compressible base portions of the tool parts are flexible and resilient enough to fit through the minimum diameter 62 of the apertures 26, 40 and the restricted orifice 76 of the alternate aperture 26a, in a tightly fitting fashion, the apertures 26, 26a and 40 can receive tool parts with a range of widths or diameters. Provided that the minimum diameters 62 of the aperture 26, 40 and the minimum diameter 70 of the alternate aperture 26a are sufficiently smaller than the width of the compressible base portions 28, 46 of the toolparts 24, 24a, 38, the apertures will secure the tool parts interior of the heads 16, 16a, 20. Also, because the compressible base portions 28, 46 are resilient, they can be removed and reinstalled. The preferred embodiment of the compressible base portions 28, 46 comprises a cylindrical shape of resilient plastic.

FIG. 5 shows an alternate embodiment of the dental tool 80. In this embodiment, the structure of the dental tool 80 is similar to the dental tool 10 as depicted in FIG. 1 except the second shaft 18, the second head 20, and the second brush 38 are deleted. Also the handle 12 is replaced by a handle 82 which has an appropriate beveled off end 84.

The preferred embodiment of the present invention (less tool parts) comprises a one piece structure composed of stainless steel. The one piece structure prevents parts from separating or coming loose during manipulation by the user. Additionally, stainless steel construction permits sterilization of the dental tool by autoclave or chemclave methods.

As is apparent from the foregoing specification, the invention is susceptible of being embodied with various alterations and modifications which may differ particularly from those that have been described in the preceding specification and description. It should be understood that we wish to embody within the scope of the patent warranted hereon all such modifications as reasonably and properly come within the scope of our contribution to the art.

We claim as our invention:

1. A dental tool comprising: an elongated handle; at least one head portion carried by said handle;
   each said head portion having a first opening and a second opening therein extending inwardly of an outer surface thereof;
   a first tool part and a second tool part having a first base portion and a second base portion respectively, said first base portion removably insertable into said first opening and said second base portion removably insertable into said second opening;
   first engagement means formed on at least one of said first opening and said first base portion to cause a gripping engagement between said first base portion and said first opening; and
   second engagement means formed on at least one of said second opening and said second base portion to cause a gripping engagement between said second base portion and said second opening, and said first and second engagement means automatically engage when the first and second base portions respectively are fully inserted into the first and second openings respectively, there being no mechanical adjustment required to cause engagement.

2. A dental tool according to claim 1, wherein said head portion is carried on a shaft-like extension of said handle.

3. A dental tool according to claim 2, wherein said shaft-like extension is angularly displaced along its length.

4. A dental tool according to claim 1, wherein said first and second openings in said head define opposite ends of a single linear passage.

5. A dental tool according to claim 1, wherein said first and second base portions are compressible and resilient.

6. A dental tool according to claim 5, wherein one of said first and second engagement means comprises a constriction of one of said first and second openings respectively, inwardly of said outer surface to a cross section at least slightly smaller than that of one of said first and second base portions, respectively.

7. A dental tool according to claim 6, wherein one of said first and second openings has walls and said constriction is formed by a constant tapering of said walls.

8. A dental tool according to claim 6, wherein one of said first and second openings has walls and said constriction is formed in said walls at a discrete distance internal of said outer surface.

9. A dental tool according to claim 1, wherein said first and second openings comprise circular cross sections and said first and second base portions comprise generally cylindrical shapes.

10. A dental tool according to claim 1, wherein said handle has a longitudinal axis and each of said first and second openings has a longitudinal axis, and an included angle between said handle longitudinal axis and the longitudinal axis of said first opening is an acute angle and an included angle between said handle longitudinal axis and the longitudinal axis of said second opening is an obtuse angle.

11. A dental tool according to claim 1, wherein said handle and said head portion are formed as one piece.

12. A dental tool according to claim 1, wherein two head portions are carried by said handle.

13. A dental tool according to claim 1, wherein said first base portion is selectively removably insertable into said second opening, and said second engagement means causes a gripping engagement between said first base portion and said second opening upon insertion, with no mechanical adjustment required to cause engagement.

14. A tool comprising:
    at least one tool part;
    a handle;
    at least one head connected to said handle, said head providing at least two openings for selectively receiving the tool part, said head comprising a gripping means interior of said two openings such that once inserted into either selected one of said two openings the tool part is held firmly therein by said gripping means, the gripping means automatically activated by the insertion of the tool part into said one of said two openings.

15. A tool as claimed in claim 14 wherein said head is offset from a longitudinal axis of said handle and said two openings in said head provide a first port for said tool part at one of said two openings and a second port for said tool part at the respective other of said two openings oriented 180° from said first port.

16. A tool as claimed in claim 14 wherein said tool part comprises a compressible, resilient base portion and said gripping means comprises a reduced width of both said two openings in an interior of said head such that said head grips said base portion of said tool part.

17. A tool as claimed in claim 14 wherein said handle, and said head comprise a one-piece structure.

18. A dental tool comprising:
    a handle;
    at least one bent shaft member, said shaft member connected at a first end to one end of said handle in a generally collinear fashion;
    at least one head, said head attached to said shaft member at a second end of said shaft member, said head having an aperture therein, said aperture extending throughout a depth of said head, said aperture having a generally linear centerline throughout, said aperture having first and second terminal open ends, said aperture having a constriction therein at a central portion of said head, said centerline of said aperture being formed at an angle approximately perpendicular to a longitudinal axis of said shaft member at said second end of said shaft member; and
    at least one tool part, said tool part comprising a compressible, resilient base portion, said base portion removably insertable interior of said head into said aperture, through an arbitrarily selected one of said first and second terminal open ends of said aperture, said base portion comprising a width that is insertable into a width of said aperture at both first and second terminal open ends, said base portion comprising a width larger than a clearance defined by said constriction interior of said head, said constriction causing said head to grip said base portion of said tool part upon full insertion of said base portion into said arbitrarily selected one of said terminal open ends.

19. A dental tool according to claim 18, wherein said aperture is tapered toward said constriction from both first and second terminal open ends.

20. A dental tool according to claim 18, wherein said aperture is generally cylindrical throughout the depth of said head except for said constriction at said central portion of said head.

21. A dental tool according to claim 18 further comprising:
a second bent shaft member, said second bent shaft member connected at a near end to a second end of said handle in a generally collinear fashion;
a second head, said second head attached to said shaft member at a far end of said shaft member, said second head having a passage therein, said passage extending throughout a depth of said second head, said passage having a generally linear center line throughout, said passage having a second constriction therein at a central portion of said second head, said center line of said passage being formed at an angle approximately perpendicular to a longitudinal axis of said second shaft member at said far end of said second shaft member; and
a second tool part, said second tool part comprising a compressible resilient second base portion, said second base portion removably insertable interior of said second head through said passage, from either terminal end of said passage, said second base portion comprising a smaller width than a width of said passage at an outside surface, said second base portion comprising a larger width than said second constriction interior of said second head, said second constriction causing said second head to grip said second base portion of said second tool part.

* * * * *